(12) United States Patent
Balthasar et al.

(10) Patent No.: US 7,662,928 B2
(45) Date of Patent: Feb. 16, 2010

(54) ANTI-FCRN ANTIBODIES FOR TREATMENT OF AUTO/ALLO IMMUNE CONDITIONS

(75) Inventors: Joseph P. Balthasar, Lancaster, NY (US); Ryan J. Hansen, Carmel, IN (US); Feng Jin, Lockport, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/634,676

(22) Filed: Dec. 6, 2006

(65) Prior Publication Data

US 2007/0092507 A1 Apr. 26, 2007

Related U.S. Application Data

(63) Continuation-in-part of application No. 10/914,403, filed on Aug. 9, 2004, now abandoned.

(60) Provisional application No. 60/762,151, filed on Jan. 25, 2006.

(51) Int. Cl.
| | |
|---|---|
| A61K 39/395 | (2006.01) |
| C07K 16/28 | (2006.01) |
| C12N 5/20 | (2006.01) |
| G01N 33/563 | (2006.01) |
| G01N 33/564 | (2006.01) |
| G01N 33/577 | (2006.01) |
| C12P 21/08 | (2006.01) |

(52) U.S. Cl. .............................. 530/388.22; 424/133.1; 424/139.1; 424/143.1; 424/144.1; 435/7.1; 435/7.21; 435/70.21; 435/452; 435/334; 436/506; 436/512; 436/547; 436/548; 530/387.3; 530/388.7; 530/389.3; 530/389.6

(58) Field of Classification Search ................. 435/7.1, 435/7.21, 70.21, 452, 334; 436/506, 512, 436/547, 548; 530/387.3, 388.22, 388.7; 530/389.3, 389.6; 424/133.1, 139.1, 143.1, 424/144.1
See application file for complete search history.

(56) References Cited

U.S. PATENT DOCUMENTS 6,992,234 B2 * 1/2006 Roopenian .................... 800/3

2002/0138863 A1 9/2002 Roopenian

FOREIGN PATENT DOCUMENTS

WO WO 2004035753 A2 4/2004

OTHER PUBLICATIONS

Roes et al., 1995. Mouse anti-mouse IgD monoclonal antibodies generated in IgD-deficient mice. J. Immunological Methods 183: 231-237.*
Getman et al., 2005. Pharmacokinetic effects of 4C9, and anti-FcRn antibody, in rats: implications for the use of FcRn inhibitors for the treatment of humoral autoimmune and alloimmune conditions. J. Pharmaceutical Sci. 94: 718-729.*
Raghavan et al., 1994. Investigation of the interaction between the class 1 MHC-related Fc receptor and its immunoglobulin G ligand. Immunity 1: 303-315.
Lampson et al., 1983. Striking paucity of HLA-A, B, C and Beta-2-microglobulin on human neuroblastoma cell lines. J. Immunol. 130: 2471-2478.
Parham et al., 1983. Arginine 45 is a major part of the antigenic determinant of human beta-2-microglobulin recognized by mouse monoclonal antibody BBM.1. J. Biol. Chem. 258: 6179-6186.
Yu et al., 1999. Mechanism of intravenous immune globulin therapy in antibody-medicated autoimmune diseases. New England Journal of Medicine 340: 227-228.
Story et al., 1994. A major histocompatibility complex class-I-like Fc receptor cloned from human placenta: possible role in transfer of immunoglobulin G from mother to fetus. J. Exp. Med. 180: 2377-2381.
Bussel, *Another Interaction of the FcR System with IVIG*, Thromb Haemost, 2002, 88, pp. 890-891.
Hansen et al., *Effects of intravenous immunoglobulin on platelet count and antiplatelet antibody disposition in rat module of immune thrombocytopenia*, Blood, Sep. 15, 2002, V. 100, No. 6, pp. 2087-2093.
Hansen et al., *Intravenous Immunoglobulin Mediates an Increase in Anti-Platelet Antibody Clearance via the FcRn Receptor*, Thromb Haemost, 2002, 88, pp. 898-899.
Hansen et al., *Pharmacokinetic/Pharmacodynamic Modeling of the Effects of Intravenous Immunoglobulin on the Disposition of Antiplatelet Antibodies in a Rat Model of Immune Thombocytopenia*, Jun. 2003, V. 92, No. 6, pp. 1206-1215.

* cited by examiner

*Primary Examiner*—Ann Y. Lam
*Assistant Examiner*—James L Grun
(74) *Attorney, Agent, or Firm*—Hodgson Russ LLP (57) ABSTRACT

Antibodies to heavy chain of human FcRn are provided which function as non-competitive inhibitors of IgG binding to FcRn. The antibodies may be polyclonal, monoclonal, chimeric or humanized, or antigen binding fragments thereof. These antibodies are useful for reducing the concentration of pathogenic IgGs in individuals and therefore used as a therapeutic tool in autoimmune and alloimmune conditions.

13 Claims, 8 Drawing Sheets

SEQUENCE LISTING

<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Gly Glu Glu Phe Met Asn Phe Asp Leu Lys Gln Gly Thr
1               5                   10

ANTI-FCRN ANTIBODIES FOR TREATMENT OF AUTO/ALLO IMMUNE CONDITIONS

This application claims priority to U.S. Provisional application No. 60/762,151, filed on Jan. 25, 2006, and is also a continuation-in-part of U.S. Non-provisional application Ser. No. 10/914,403, filed on Aug. 9, 2004, now abandoned the disclosures of which are incorporated herein by reference.

This work was supported by Grant No. HL 067347 and AI60687 from the National Institutes of Health. The Government has certain rights in the invention.

FIELD OF THE INVENTION

The present invention relates generally to the field of autoimmune and alloimmune diseases.

BACKGROUND OF THE INVENTION

Humoral autoimmune and alloimmune conditions are mediated by pathogenic antibodies. Some examples of autoimmune diseases include immune neutropenia, myasthenia gravis, multiple sclerosis, lupus and immune thrombocytopenia (ITP).

ITP is primarily a disease of increased peripheral platelet destruction, where most patients develop antibodies that bind to specific platelet membrane glycoproteins. The anti-platelet antibodies effectively opsonize platelets, leading to rapid platelet destruction by cells of the reticulo-endothelial system (e.g., macrophages). Relative marrow failure may contribute to this condition, since studies show that most patients have either normal or diminished platelet production. In general, attempts to treat ITP include suppressing the immune system, and consequently causing an increase in platelet levels.

ITP affects women more frequently than men, and ITP is considered to be an autoimmune disease that is common in children and adults. The incidence is 1 out of 10,000 people. In the US, the incidence of ITP in adults is approximately 66 cases per 1,000,000 per year. An average estimate of the incidence in children is 50 cases per 1,000,000 per year. Internationally, childhood ITP occurs in approximately 10-40 cases per 1,000,000 per year.

This problem is significant because chronic ITP is one of the major blood disorders in both adults and children. It is a source of significant hospitalization and treatment cost at specialized hematological departments in the US and around the world. Each year there are approximately 20,000 new cases in the US, and the cost for ITP care and special therapy is extremely high.

Most children with ITP have a very low platelet count that causes sudden bleeding, with typical symptoms including bruises, small red dots on the skin, nosebleeds and bleeding gums. Although children can sometimes recover with no treatment, many doctors recommend careful observation and mitigation of bleeding and treatment with intravenous infusions of gamma globulin.

Intravenous administration of human immunoglobulin (IVIG) in large amounts has been shown to increase platelet counts in children afflicted with immune ITP, and IVIG has shown to be beneficial as a treatment for several other autoimmune conditions.

Many studies have investigated the mechanisms by which IVIG achieves effects in the treatment of autoimmune diseases. With regard to ITP, early investigations led to the conclusion that IVIG effects are mainly due to blockade of the Fc receptors responsible for phagocytosis of antibody-opsonized platelets. Subsequent studies showed that Fc-depleted IVIG preparations provided increases in platelet counts in some patients with ITP, and recently it was reported that IVIG effects are due to stimulation of FcγRIIb expression on macrophage cells, leading to inhibition of platelet phagocytosis. Such IVIG treatments, however, have substantial side effects and are very costly to develop and administer. Further, other therapies used for the treatment of autoimmune/alloimmune conditions other than IVIG include polyclonal anti-D immunoglobulin, corticosteroids, immuno-suppressants (including chemotherapeutics), cytokines, plasmapheresis, extracorporeal antibody adsorption (e.g., using Prosorba columns), surgical interventions such as splenectomy, and others. However, like IVIG, these therapies are also complicated by incomplete efficacy and high cost.

Recently, it has been proposed to raise anti-human FcRn antibodies in knock-out mice lacking the FcRn gene (Roopenian, 2002, U.S. publication no. 2002/138863). The author argues that high affinity antibodies that bind to the same epitope of FcRn as IgG would competitively inhibit the binding of pathogenic IgG to FcRn and therefore increase clearance. However, no such antibodies were demonstrated and therefore the efficacy of such antibodies is still in question. Moreover, owing to the high affinity of endogenous IgG to FcRn and to the high concentrations of endogenous IgG in blood, it is likely that competitive inhibition of FcRn would require very high doses and therefore may be associated with similar side effects as the current IVIG treatment.

Based on the state of the prior art, there is substantial need for the development of new therapies for autoimmune and alloimmune conditions that do not have the low potency and high cost of IVIG. It is therefore desirable to identify a safer and more effective alternative to IVIG for treatment for autoimmune and alloimmune conditions.

SUMMARY OF THE INVENTION

This invention provides compositions and methods for treatment of autoimmune and alloimmune conditions. The compositions of the present invention comprise agents which function non-competitively to inhibit the transport of IgG by FcRn receptors. Non-competitive receptor inhibitors, by definition, demonstrate inhibitory activity that is independent of the concentration of the receptor ligand (e.g., IgG). With regard to FcRn-mediated transport of IgG, non-competitive inhibition may be achieved by non-competitive binding of inhibitors to FcRn at physiological pH, and incomplete dissociation of the inhibitor-FcRn complex during the time-course of endosomal sorting and transit. Alternatively, or additionally, non-competitive inhibition may be achieved by binding to a site that is distant from, and/or not identical to, the ligand binding site. The antibodies of the present invention bind to the FcRn such that binding of pathogenic antibodies to the FcRn is inhibited thereby improving the clearance of the pathogenic antibodies from an individual's body. In one embodiment, the agents which binds to FcRn are polyclonal or monoclonal antibodies directed to the heavy chain or the light chain of the FcRn. In one embodiment, the present invention provides polyclonal and monoclonal antibodies to the human FcRn receptors. In another embodiment, the antibodies are chimeric or humanized.

The invention also provides a method for ameliorating an autoimmune or alloimmune condition comprising administering to an individual a composition comprising an agent which functions as a non-competitive inhibitor of IgG for binding to FcRn and which binds to the FcRn such that binding of pathogenic antibodies to the FcRn is inhibited. In different embodiments, the agent is polyclonal, monoclonal, chimeric or humanized antibodies directed to FcRn, particularly human FcRn receptors. In another embodiment, the antibodies are directed to the heavy chain of the FcRn receptor.

BRIEF DESCRIPTION OF FIGURES

FIG. 1. IVIG effects on the time course of 7E3-induced thrombocytopenia. Rats received IVIG (or saline) followed by 8 mg/kg 7E3. Panel A. Individual raw platelet count versus time data for animals given saline (1), 0.4 g/kg IVIG (2), 1 g/kg IVIG (3), or 2 g/kg IVIG (4). Panel B. Average percent of initial platelet count data. Symbols represent IVIG treatment groups (n=4 rats/group): saline (●), 0.4 g/kg (■), 1 g/kg (▲), and 2 g/kg (♦). IVIG and 7E3 were given intravenously, and platelet counts were obtained using a Cell-Dyne 1700 multi-parameter hematology analyzer. Error bars represent the standard deviation about the mean. IVIG attenuated the time-course of thrombocytopenia in a dose-dependent manner. Treatments differences were statistically significant (p=0.031).

FIG. 2. Plasma 7E3 pharmacokinetics following IVIG treatment. Rats (3-4 per group) were dosed intravenously with IVIG (0-2 g/kg) followed by 7E3 (8 mg/kg). Panel A shows plasma 7E3 pharmacokinetic data for each animal given saline (1), 0.4 g/kg IVIG (2), 1 g/kg IVIG (3), or 2 g/kg IVIG (4). Panel B. Average plasma pharmacokinetic data for animals receiving 7E3 and IVIG. Treatment groups are designated as follows: saline (●), 0.4 g/kg (■), 1 g/kg (▲), and 2 g/kg (♦). 7E3 concentrations were determined via ELISA. Error bars represent the standard deviation about the mean concentration at each time point. IVIG treatment significantly increased the clearance of 7E3 (p<0.001), calculated from the concentration vs. time profiles shown in this figure.

FIG. 3. IVIG does not directly bind 7E3. 7E3 (or control IgG) and IVIG were combined in vitro, at a constant IVIG concentration (25 mg/ml) and varying 7E3 concentrations (0-0.1 mg/ml). The positive control was a mouse anti-human IgG. Samples were then added to a microplate coated with anti-human IgG. Murine IgG binding was visualized using a secondary anti-mouse IgG-alkaline phosphatase conjugate. p-Nitro phenyl phosphate was added, and the plates were read at 405 nm (kinetic assay, over 10 min). Assay response to 7E3 did not differ from control (p=0.164), whereas the positive control differed significantly from control (p<0.001).

FIG. 4. Plasma AMI pharmacokinetics following IVIG treatment. Rats (3 per group) were dosed intravenously with saline (●) or 2 g/kg (♦) IVIG, followed by AMI (8 mg/kg). AMI concentrations were determined via ELISA. Error bars represent the standard deviation about the mean concentration at each time point. IVIG treatment significantly increased the clearance of AMI (p<0.001), calculated from the concentration vs. time profiles shown in this figure. IVIG's effects on antibody pharmacokinetics are not specific for 7E3.

FIG. 6. IVIG effects on the 7E3-platelet binding curve. Total platelet concentration was held constant as the 7E3 concentration was increased, in the presence (○) or absence (▽) of IVIG. Free (i.e., unbound) 7E3 concentrations were determined by ELISA. Data were fit as described in the text. The lines represent the best fits of the data sets (solid line=IVIG, broken line=no IVIG), and are essentially superimposed. Parameters ($K_A$ and $R_t$) obtained from the fits did not differ significantly. Without IVIG present, $K_A$ was $4.9 \pm 0.7 \times 10^8 M^{-1}$, and $R_t$ was $7.5 \pm 0.4 \times 10^{-8}$ M ($55000 \pm 3000$ GP/platelet). With IVIG, $K_A$ was $5.5 \pm 1.2 \times 10^8 M^{-1}$, and $R_t$ was $7.6 \pm 0.7 \times 10^{-8}$ M ($56000 \pm 5000$ GP/platelet). IVIG does not prevent 7E3 from binding to platelets.

FIG. 9. Plasma AMI pharmacokinetics following different doses of 4C9. Rats (3-4) per group were dosed intravenously with 4C9 (0-60 mg/kg) four hours before administration of AMI (8 mg/kg i.v.). Blood samples were collected, and plasma samples were analyzed for AMI concentrations via ELISA. Treatment groups are designated as follows: saline (●), 3 mg/kg (■), 15 mg/kg (▲), 60 mg/kg (♦). Error bars represent standard deviation about the mean AMI concentration at each point. The 15 and 60 mg/kg significantly increased (p<0.01) the clearance of AMI compared to control.

FIG. 10. Reactivity of hybridoma supernatant against human FcRn. Hybridomas were generated which secrete antibodies against the light chain of hFcRn. Plates were coated with the light chain of human FcRn and incubated with supernatants from the indicated hybridomas. Goat anti-mouse Fab fragment conjugated to alkaline phosphatase was used to identify positive clones. Eight hybridomas producing antibodies specific for the light chain of human FcRn were identified.

DETAILED DESCRIPTION OF THE INVENTION

The term "pathogenic antibodies" as used herein refers to antibodies that beget morbid conditions or disease. Such antibodies include anti-platelet antibodies.

The present invention provides compositions and methods for increasing the clearance of pathogenic antibodies. These compositions and methods are useful for treatment of autoimmune and alloimmune conditions. The compositions and methods of the present invention are directed to binding FcRn (also known as: Fc-receptor of the neonate, FcRP, FcRB, and the Brambell Receptor) in a manner sufficient to prevent pathogenic antibodies from binding FcRn.

In the present invention are provided specific anti-FcRn therapies. The majority of inhibitors of enzymes or receptors act as competitive inhibitors of substrate or ligand binding such that the inhibitor binds to the same site on the receptor as the ligand and therefore the degree of inhibition is a direct function of the relative affinities and concentrations of the inhibitor and ligand. U.S. patent application no. 2002/0138863 to Roopenian (see paragraph 0031) emphasizes that the antibodies to the FcRn should bind the FcRn at the same site that is critical for binding of IgG to Fc so that when the antibody is bound to FcRn, the binding of IgG to that site of FcRn is inhibited. With the emphasis in the prior art being directed to competitive inhibitors, it was surprisingly observed in the present invention that non-competitive inhibitors of IgG for binding to FnRn would have therapeutic value.

Further, Roopenian et al. acknowledge it is difficult to produce high specificity anti-FcRn antisera (see paragraph 0085). This reference proposes to overcome this problem by generation of anti-FcRn antibodies in FcRn deficient mice so that FcRn would be recognized as a foreign molecule. However, in the present invention, we have been able to produce high affinity and specificity antibodies to both the light chain and the heavy chain of FcRn by immunizing animals repetitively with the human FcRn light chain and with a novel immunoconjugate comprised of a human FcRn heavy chain peptide fragment covalently linked to keyhole limpet hemocyanin.

In a preferred embodiment, the antibodies or fragments thereof are non-competitive inhibitors of IgG binding to, or transport by, human FcRn. The antibodies or fragments may be of any isotype (e.g., IgA, IgD, IgE, IgG, IgM, etc.), and the antibodies may be generated in any species (e.g., mouse, rat, etc.). Depending on the species of origin (see Ober et al., 2001, Int Immunol 13:1551-9), antibodies of the IgG isotype may competitively inhibit the binding of IgG to human FcRn. Such antibodies can be used, provided that they also act as non-competitive inhibitors of IgG binding to FcRn. That is, an antibody that is both a non-competitive and a competitive inhibitor of IgG binding to FcRn may be used.

FcRn binds its ligand (i.e., IgG) with pH dependent affinity. It shows virtually no affinity for IgG at physiologic pH. Accordingly, anti-FcRn antibodies that bind FcRn at physiologic pH (7.0 to 7.4) may act as non-competitive inhibitors, such that the binding of the anti-FcRn antibody to FcRn is not influenced by the presence of IgG. The ability of the antibodies of the present invention to bind to FcRn in a pH-independent manner in the range of pH 6 to 8 and also in a non-competitive manner allows functional inhibition of FcRn-mediated transport of IgG at concentrations much lower than those required for competitive inhibitors. While not intending to be bound by any particular theory, it is hypothesized that pH independence in the range of pH 6-8 allows such inhibitors to bind to FcRn on the cell surface (physiological pH), and to remain bound to FcRn during the course of intracellular transit, thereby inhibiting FcRn binding to IgG within endosomes at acidic pH (~6). The non-competitive mode of binding allows these inhibitors to be used at much lower concentrations than competitive inhibitors making them attractive for therapeutic purposes. While not intending to be bound by any particular theory, it is considered that the result is to inhibit FcRn-mediated protection of IgG from intracellular catabolism thereby leading to an increase in the clearance of IgG As demonstrated herein in the examples, IVIG mediates a dose-dependent increase in elimination of pathogenic antibody in animal models of ITP, and this effect is mediated by IVIG interaction with FcRn. However, very high doses of IVIG are required to produce substantial increases in the clearance of pathogenic antibody (i.e., the typical clinical dose of IVIG is 2 g/kg) in part due to the putative mechanism of IVIG inhibition of FcRn binding with pathogenic antibody (i.e., competitive inhibition), and in part due to the fact that IgG shows very low affinity for FcRn at physiologic pH (i.e., pH 7.2-7.4).

The present invention is for specific anti-FcRn therapies that provide non-competitive inhibition of FcRn binding to pathogenic antibodies at physiologic pH and allow non-competitive inhibition of FcRn binding to pathogenic antibodies. Thus, the present invention provides a method of preventing pathogenic antibodies from binding FcRn as a treatment for autoimmune and alloimmune disorders. The present method also provides compositions useful for specifically inhibiting FcRn in a manner sufficient to prevent pathogenic antibodies from binding FcRn. The compositions and methods of the present invention preferably effect, in the recipient of the treatment, both an increase in the rate of elimination of pathogenic antibodies and palliation of morbidity and disease caused by the pathogenic antibodies.

In one embodiment the present invention provides anti FcRn (heavy chain) antibodies. These antibodies can be generated by using the whole heavy chain or peptides corresponding to sequences of the heavy chain. Examples of such antibodies are presented in Examples 12-15. The antibodies were observed to not bind to b2 microglobulin. However, since they bind to the FcRn complex (comprising both the heavy chain and the b2 microglobulin) and were generated against a sequence of the heavy chain of FcRn, it is most likely that these antibodies bind to the heavy chain of human FcRn.

The compositions and methods of the present invention are accordingly suitable for use with autoimmune disorders including but not limited to immune cytopenias, immune neutropenia, myasthenia gravis, multiple sclerosis, lupus and other conditions where antibodies cause morbidity and disease. In addition to humans, the antibodies of the present invention can be used in other species also.

The compositions of the present invention comprise an agent that can inhibit FcRn from binding pathogenic antibodies such as anti-platelet antibodies. Such compositions include but are not limited to monoclonal antibodies, polyclonal antibodies and fragments thereof. The antibodies may be chimeric or humanized, antibody fragments, peptides, small-molecules or combinations thereof that can prevent pathogenic antibodies from binding the FcRn receptor. Antibody fragments that include antigen binding sites may also be used. Such fragments include, but are not limited to, Fab, F(ab')$_2$, Fv, and single-chain Fv (i.e., ScFv). Such fragments include all or part of the antigen binding site and such fragments retain the specific binding characteristics of the parent antibody.

The antibodies of the present invention may be chimeric antibodies, humanized antibodies. "Chimeric" antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to human constant (C) segments. Such a chimeric antibody is likely to be less antigenic to a human than antibodies with mouse constant regions as well as mouse variable regions.

"Humanized" antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins in which residues from a complementary determining region (CDR) are replaced by residues from a CDR of a non-human species such as mouse, rat or rabbit having the desired specificity, affinity and capacity. In some instances, Fv framework residues of the human immunoglobulin are replaced by corresponding non-human residues. Humanized antibodies may also comprise residues which are found neither in the human antibody nor in the non-human imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

Methods for humanizing non-human antibodies are well known in the art. Generally, a humanized antibody has one or more amino acid residues introduced into it from a source which is non-human. These non-human amino acid residues can be referred to as "import" residues, which are typically taken from an "import" variable domain. Humanization can be essentially performed following the method of Winter and co-workers (Jones et al., Nature, 321:522 525 (1986); Riechmann et al., Nature, 332:323 327 (1988); Verhoeyen et al. Science, 239:1534 1536 (1988)), by substituting rodent CDRs or CDR sequences for the corresponding sequences of a human antibody. In practice, humanized antibodies are typically human antibodies in which some CDR residues and possibly some FR residues are substituted by residues from analogous sites in rodent antibodies.

Polyclonal antibodies directed to FcRn or a fragment thereof such as the light chain or the heavy chain can be prepared by immunizing a suitable subject with FcRn or portions thereof such as the light chain, the heavy chain, and peptide sections included within the molecule. The anti-FcRn or a fragment thereof antibody titer in the immunized subject can be monitored over time by standard techniques, such as ELISA using immobilized FcRn or a fragment thereof. If desired, the antibody molecules directed against FcRn or a fragment thereof can be isolated from the mammal (e.g., from the blood) and further purified by well known techniques, such as protein A chromatography to obtain the IgG fraction.

Monoclonal antibodies directed toward FcRn or a fragment thereof can also be produced by standard techniques, such as the hybridoma technique originally described by Kohler and Milstein (1975, Nature 256:495-497). Briefly, an immortal cell line (typically a myeloma) is fused to lymphocytes (typically splenocytes) from a mammal immunized with FcRn or a fragment thereof, and the culture supernatants of the resulting hybridoma cells are screened to identify a hybridoma producing a monoclonal antibody that binds FcRn. Typically, the immortal cell line (e.g., a myeloma cell line) is derived from the same mammalian species as the lymphocytes. Hybridoma cells producing a monoclonal antibody of the invention are detected by screening the hybridoma culture supernatants for antibodies that bind FcRn using standard ELISA assay. Human hybridomas can be prepared in a similar way.

An alternative to preparing monoclonal antibody-secreting hybridomas is to identify and isolate monoclonal antibodies by screening a recombinant combinatorial immunoglobulin library (e.g., an antibody phage display library) with FcRn or a fragment thereof.

Administration of the compositions of the present invention can be carried out by methods known to those skilled in the art. When the specific inhibitor of FcRn comprises an antibody, administration may be carried out by, for example, intravenous, intramuscular or subcutaneous injection, cannula or other methods known to those skilled in the art. Similarly, administration of small molecules effective to prevent binding of anti-platelet antibodies to FcRn receptors can be carried out by methods well known to those skilled in the art.

For the elimination of pathogenic antibodies in the treatment of autoimmune and alloimmune conditions, the inhibitor antibody or antibodies of the present invention can be administered. It will be appreciated by those skilled in the art that the effects of the inhibitor antibodies on the elimination of pathogenic antibodies in a particular individual will likely be dependent on the dosing regimen, the pharmacokinetics of the inhibitor antibodies (i.e., the rate and extent of inhibitor distribution and elimination), the affinity of the inhibitor antibodies for FcRn, the transport capacity of FcRn and, potentially, on the turnover of the FcRn receptor. Animal studies presented herein have demonstrated that a model inhibitor antibody led to a dose-dependent, transient increase in IgG elimination in rats. It is believed that the transient nature of the effect may allow control of the duration of FcRn blockade, and may allow minimization of any risks associated with FcRn blockade (e.g., risk for infection).

The pH 6 to 8 independent and non-competitive inhibitors of the present invention should cause parallel decreases in the concentrations of endogenous pathogenic and non-pathogenic IgG antibodies. As such, the influence of high affinity, non-competitive inhibitors of FcRn on pathogenic antibody concentrations may be estimated based on the effects of the inhibitors on total serum concentrations of endogenous IgG. The FcRn inhibitors may be administered as single and/or multiple-doses. Generally, 1-2000 mg/kg, preferably 1-200 mg/kg, and a more preferably, 1-40 mg/kg may be administered to patients afflicted with autoimmune or alloimmune conditions, and these regimens are preferably designed to reduce the serum endogenous IgG concentration to less than 75% of pretreatment values. Intermittent and/or chronic (continuous) dosing strategies may be applied.

While the present invention is illustrated by way of the following examples, the examples are meant only to illustrate particular embodiments of the present invention and are not meant to be limiting in any way.

Example 1

This example describes the general methods used. Female Sprague-Dawley rats, 200 to 225 g, were used for the in vivo analyses. Rats were instrumented with jugular vein catheters 2 days prior to treatment. 7E3, a murine antiglycoprotein IIb/IIIa (GPIIb/IIIa) monoclonal antibody, was produced from hybridoma cells obtained from American Type Culture Collection (Manassas, Va.). Hybridoma cells were grown in serum-free media (Life Technologies®, Rockville, Md.) and antibodies were purified from the media using protein G chromatography. IVIG preparations were obtained from Baxter Healthcare® (Hyland Division, Glendale, Calif.) and Bayer® (Pharmaceutical Division, Elkhart, Ind.). Both IVIG preparations are solvent/detergent-treated and are manufactured via cold ethanol fractionation of human plasma. Outdated human platelets were obtained from the American Red Cross (Buffalo, N.Y. and Salt Lake City, Utah). A murine antimethotrexate IgG1 monoclonal antibody (AMI) was generated and purified in our laboratory. Goat antihuman IgG (no cross-reactivity to goat and mouse serum proteins) and alkaline phosphatase—conjugated goat antimouse IgG (no cross-reactivity to goat and human serum proteins) were both obtained from Rockland (Gilbertsville, Pa.). Mouse antihuman IgG, fluorescein isothiocyanate (FITC)—labeled anti-mouse IgG, and p-nitrophenyl phosphate were from Pierce® (Rockford, Ill.). Bovine serum albumin (BSA) and buffer reagents were obtained from Sigma® (St Louis, Mo.). Buffers were phosphate-buffered saline (PBS, pH 7.4), 0.02 M Na2HPO4 (PB), and PB plus 0.05% Tween-20 (PB-Tween).

Examples 2-5 illustrate the effect IVIG on antiplatelet antibody. These examples illustrates that IVIG is able to attenuate the effects of an antiplatelet antibody in a rat model of ITP in a dose-dependent manner, and that IVIG has a dramatic, and apparently nonspecific, effect on antiplatelet antibody clearance.

Example 2

This example demonstrates that administration of IVIG clears anti-platelet antibodies in a rat model of IPT. Rats were dosed with IVIG (0.4, 1, or 2 g/kg) via the jugular vein catheter. Following IVIG dosing, a blood sample (0.15 mL) was withdrawn for a baseline measurement of platelet counts. Rats were then dosed with an anti-platelet antibody, 7E3, 8 mg/kg, and platelet counts were taken over 24 hours, using a Cell-Dyne 1700 multiparameter hematology analyzer (Abbott Laboratories®, Abbott Park, Ill.). Control animals were dosed with saline, followed by 7E3. The platelet nadir for each animal was the lowest observed platelet count. Platelet count data were normalized by the initial platelet count because of large interanimal variability in initial platelet counts. By normalizing the data, the effects of 7E3 and IVIG can be better compared between animals. Blood samples (0.15 mL) were taken for pharmacokinetic analysis at 1, 3, 6, 12, 24, 48, 96, and 168 hours after 7E3 dosing. 7E3 plasma concentrations were determined using an enzyme-linked immunosorbent assay (ELISA) as follows. Human GPIIb/IIIa was diluted 1:500 in PB, and added to Nunc Maxisorp plates (0.25 ml/well). Plates were incubated overnight at 4° C. Standards and samples were then added to the plate (0.25 ml/well) and allowed to incubate for 45 minutes at room temperature. Finally, p-nitro phenyl was added (4 mg/m; in DEA) and the change in absorbance versus time was recorded with a SpectraMax Microplate reader. Plates were washed 3 times with PB-Tween between each step of the assay. Standards were made to final concentrations of 0, 1, 2, 2.5, 5, 10 and 20 ng/ml 7E3 in 1% mouse plasma. Intra-assay variability was <15% for quality control samples within the standard range curve.

Figure 1:
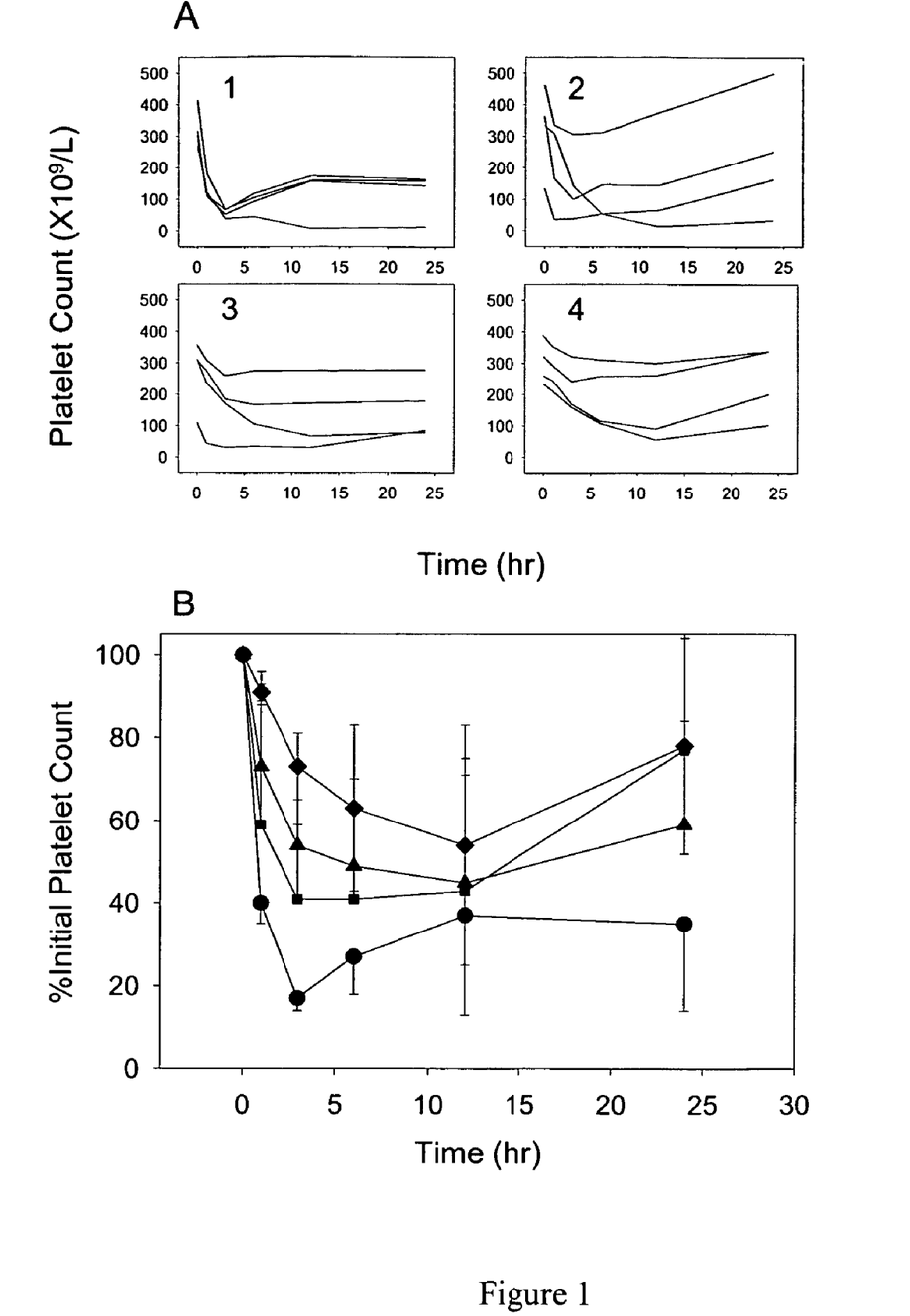

At a dose of 8 mg/kg, 7E3 caused rapid and severe thrombocytopenia in the rats. As can be seen in FIG. 1, pretreatment of rats with IVIG significantly altered the platelet count time course following the dose of 7E3 (P=0.031). Statistically significant differences from control (P<0.01) were seen in platelet counts at 1 and 3 hours for the 2-g/kg IVIG group, and at 3 hours for the 1-g/kg IVIG group. Percent platelet counts were used to assess the effects of 7E3 in this model because of the large degree of variability in initial absolute platelet counts. However, each group had comparable mean initial platelet counts, with control, 0.4-, 1-, and 2-g/kg IVIG groups having absolute initial counts of 326±62, 323±137, 272±111, and 301±69×10$^9$ platelets/L, respectively. Because absolute platelet count may be important in assessing bleeding risk, we also looked at platelet count nadir values as a metric to determine IVIG effects in this model. After 7E3 treatment alone, the animals reached an absolute platelet nadir of 48±28×10$^9$ platelets/L, which corresponded to an average of 14%±8% of initial counts. With IVIG pretreatment, a 121% to 279% increase in the nadir percent platelet count (compared to control) was observed (P=0.044), with values of 31%±26%, 44%±24%, and 53%±27% for the 0.4-, 1-, and 2-g/kg IVIG doses, respectively. Each IVIG-treated group differed significantly from the control (P<0.05). However, IVIG was not completely effective at blocking thrombocytopenia, even at the highest doses. The percentage of rats reaching a threshold value of thrombocytopenia (<30% of initial counts) decreased with dose for animals pretreated with IVIG, with 75%, 50%, and 25% of rats in the 0.4-, 1-, and 2-g/kg IVIG groups having nadir platelet counts less than 30% of initial.

These results indicate that pretreatment of the rats with IVIG attenuated 7E3-induced thrombocytopenia. IVIG pretreatment reduced the average degree of thrombocytopenia achieved after 7E3 treatment (as measured by average percent platelet count at nadir) and decreased the fraction of animals demonstrating severe thrombocytopenia.

Example 3

Figure 2:
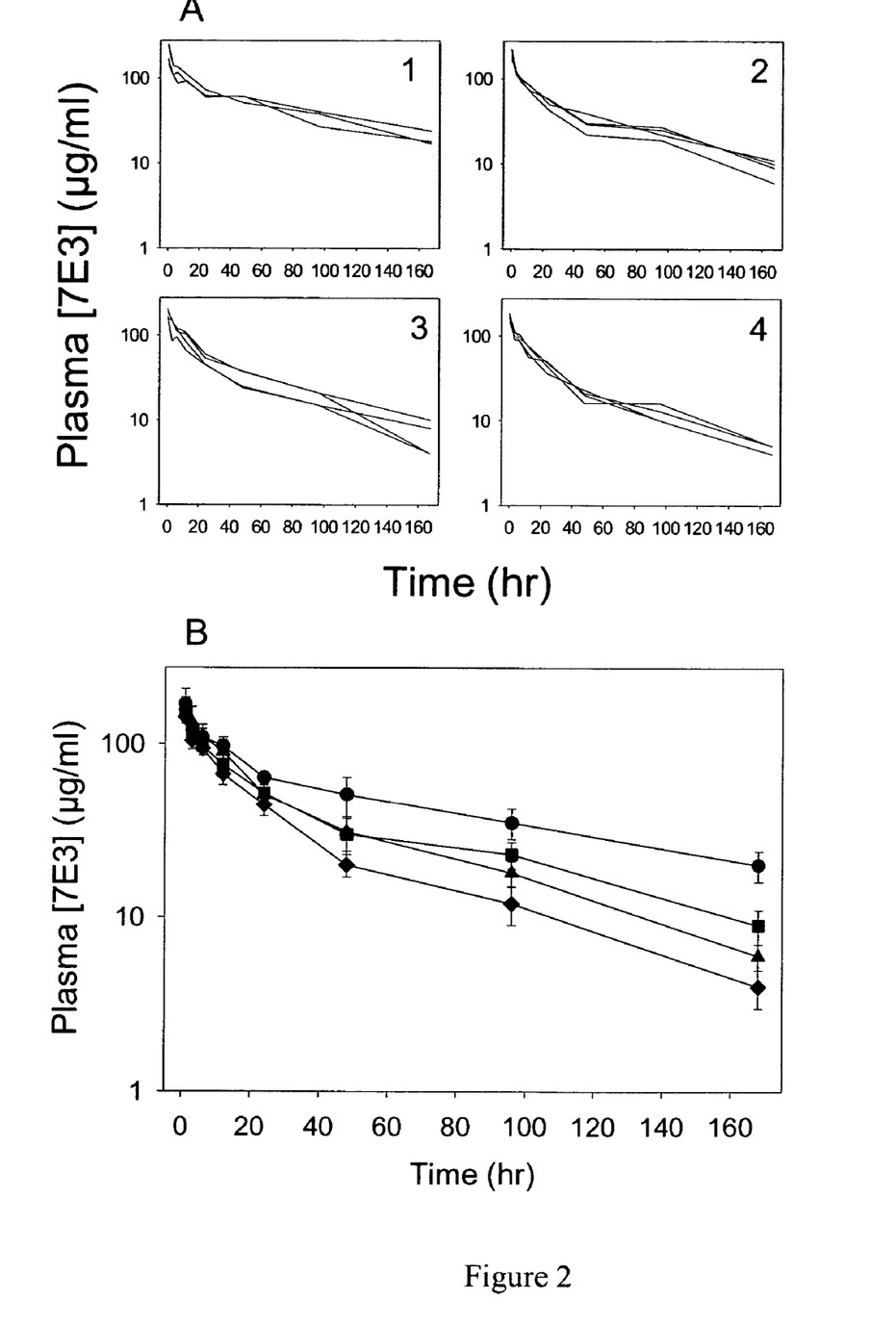

This example describes the pharmacokinetic of the effects of IVIG on 7E3. To determine this, 7E3 plasma concentrations following pretreatment of the rats with IVIG were measured. It was observed that IVIG enhanced the clearance of 7E3, as can be seen from FIG. 2 and Table 1. An ANOVA revealed highly significant differences between the clearance values calculated for the 4 treatment groups (P<0.001). Differences in 7E3 clearance were shown to be statistically significant for all pairs of treatment groups, except for the comparison of data from animals receiving 0.4 versus 1 g/kg IVIG (Tukey multiple comparisons test). Significant differences from control were seen in 7E3 concentrations at each time point at 12 hours and longer for the 2-g/kg IVIG group, and at least 48 hours for the 0.4- and 1-g/kg IVIG groups.

TABLE 1

Effect of IVIG on the elimination of 7E3

| Dose of IVIG, g/kg | Clearance of 7E3, mL h$^{-1}$kg$^{-1}$* | $t_{1/2}$, h† |
|---|---|---|
| 0 | 0.78 ± 0.09 | 79 ± 11 |
| 0.4 | 1.28 ± 0.19‡ | 68 ± 6 |

TABLE 1-continued

Effect of IVIG on the elimination of 7E3

| Dose of IVIG, g/kg | Clearance of 7E3, mL h$^{-1}$kg$^{-1}$* | t$_{1/2}$, h† |
|---|---|---|
| 1 | 1.37 ± 0.28§ | 54 ± 17‡ |
| 2 | 1.85 ± 0.19§ | 56 ± 10 |

Noncompartmental techniques were used to determine each parameter value. Values are listed as mean ± SD (n = 3–4).
*ANOVA, P < .001.
†ANOVA, P = .06.
‡Dunnett posttest, P < .05 relative to control.
§Dunnett posttest, P < .01 relative to control.

As demonstrated by this Example, IVIG altered the pharmacokinetics of 7E3. Our data demonstrated a trend toward a reduction of 7E3 terminal half-life with IVIG administration (P=0.06), with statistical significance reached in the comparison of half-life in control animals to that seen in animals receiving 1 g/kg IVIG (P<0.05). More importantly, IVIG was found to induce a dramatic increase in the clearance of the antiplatelet antibody (P<0.001). Clearance, which serves as a time-and-concentration-averaged measure of 7E3 elimination, is a better metric for evaluation of IVIG effects on 7E3 elimination, because IVIG effects on elimination rate (and half-life) may be expected to decrease with time following IVIG administration.

Example 4

This example demonstrates that IVIG does not bind to anti-FcRn antibody. Goat antihuman IgG (diluted 1:500 in PB, 0.25 mL/well) was added to the wells of a Nunc® Maxisorp® 96-well microplate (Nunc® model no. 4-42404, Roskilde, Denmark), and the plate was allowed to incubate at 4° C., overnight. IVIG (25 mg/mL) and 7E3 (0, 0.01, 0.05, and 0.10 mg/mL) were combined in test tubes and allowed to incubate for 2 hours at 37° C. Positive control samples consisted of IVIG incubated with mouse antihuman IgG (Pierce®), at the same concentrations as indicated for 7E3. Samples and controls were diluted by 1000 into 1% BSA, in PBS, and then added to the microplate (0.25 mL/well) and allowed to incubate for 2 hours at room temperature. Alkaline phosphatase-labeled antimouse IgG (diluted 1:500 in PB, 0.25 mL/well) was then added to the plate and allowed to incubate for 45 minutes, also at room temperature. Finally, p-nitrophenyl phosphate (4 mg/mL in diethanolamine buffer, pH 9.8) was added, 0.2 mL/well, and the plate was read at 405 nm on a plate reader (Spectra Max® 340PC, Molecular Devices®, Sunnyvale, Calif.). The plate was read over a period of 10 minutes, and the slopes of the absorbance verses time curves were used to assess assay response (dA/dt). Each sample was assayed in triplicate, and responses are shown as mean±SD. Between each step of the assay, the wells of the microplate were washed 3 times with PB-Tween.

Figure 3:
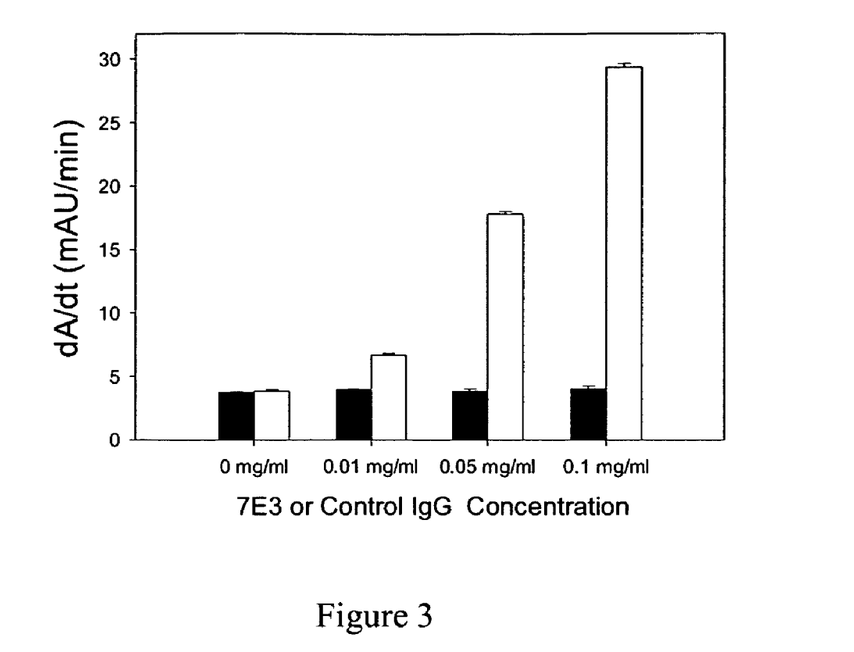

Binding of 7E3 to IVIG, in vitro, could not be detected. FIG. 3 shows the results obtained from the experiment designed to detect 7E3-IVIG binding. IVIG and 7E3 were incubated, in vitro, at 37° C., for 2 hours. Following this incubation, the samples were diluted and added to a microplate coated with antihuman IgG. Thus, if 7E3 did bind to IVIG, a secondary antimouse IgG would detect the presence of 7E3. There were no statistically significant differences between assay responses for 7E3-containing samples verses the negative control (IVIG alone), with P=0.164. However, there were significant differences in assay responses (at each concentration) for the positive control antibody, with P<0.001. The concentration ratios of 7E3/IVIG in this experiment were designed to be similar to what would be expected in the in vivo experiments.

Figure 4:
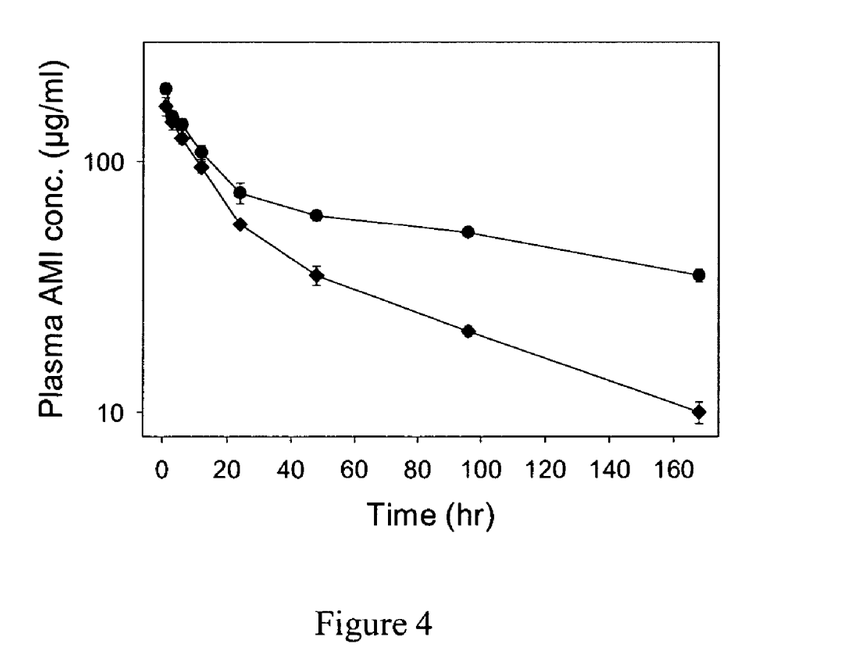

To determine if this effect of IVIG was specific for the anti-platelet antibody, 7E3, we characterized the pharmacokinetics of a second monoclonal antibody, AMI, in the presence and absence of IVIG. Rats (n=3/group) were dosed via the jugular vein cannula with 2 g/kg IVIG (or saline for controls), followed by AMI (8 mg/kg). Blood samples were taken over 1 week, and plasma was analyzed for AMI concentrations via ELISA. Pharmacokinetic analyses were performed as described above for 7E3. FIG. 4 demonstrates that IVIG also increased the clearance of AMI, with AMI clearance increasing from 0.44±0.05 to 1.17±0.05 mL hour$^{-1}$kg$^{-1}$ from the control to the IVIG-treated group (P<0.001). Furthermore, the relative degree of increased clearance due to IVIG treatment was similar between groups, with a 2.37-fold increase in clearance seen for 7E3, and a 2.66-fold increase in clearance seen for AMI, following 2-g/kg IVIG treatment.

Example 5

This example describes qualitative and quantitative studies to determine if IVIG could inhibit the binding of 7E3 to human platelets. In a qualitative study, 10 μg/mL 7E3 was incubated for 1.5 hours with human platelets (1×10$^7$ platelets/mL) in the presence or absence of IVIG (2.5 mg/mL). Control mouse IgG was a negative control. The samples were centrifuged at 4000 rpm for 6 minutes, washed with PBS (twice), and then incubated for 45 minutes with 100 μL of a 1:10 dilution (in PBS) of FITC-labeled antimouse IgG solution. Samples were washed again, resuspended in PBS, and submitted for analysis by flow cytometry (Flow Cytometry Core Facility, Huntsman Cancer Institute, Salt Lake City, Utah). In quantitative inhibition studies, the potential for IVIG inhibition of 7E3-platelet binding was studied in greater detail. Human platelets (8.2×10$^8$/mL) were incubated with 7E3 (4.8-72.5 μg/mL) in the presence or absence of IVIG (25 mg/mL), for 2 hours. Samples were then centrifuged at about 3000 g for 6 minutes to obtain a platelet pellet. A portion of each supernatant was obtained and assayed for unbound 7E3 concentration. Binding of 7E3 to platelets, in the presence and absence of 7E3, was analyzed by fitting the data to the following binding curve:

$$F_f = \frac{[7E3]_f \times K_A + 1}{1 + K_A \times [7E3]_f + K_A \times R_t}$$

In the above equation, $F_f$ is the free fraction of 7E3, $K_A$ is the apparent for 7E3-platelet binding, $[7E3]_f$ is the unbound molar 7E3 concentration, and $R_t$ is the total receptor concentration. Micromath Scientist® was used to generate nonlinear least squares analyses of the data, and parameter values and reported SDs are from the software output.

Figure 5:
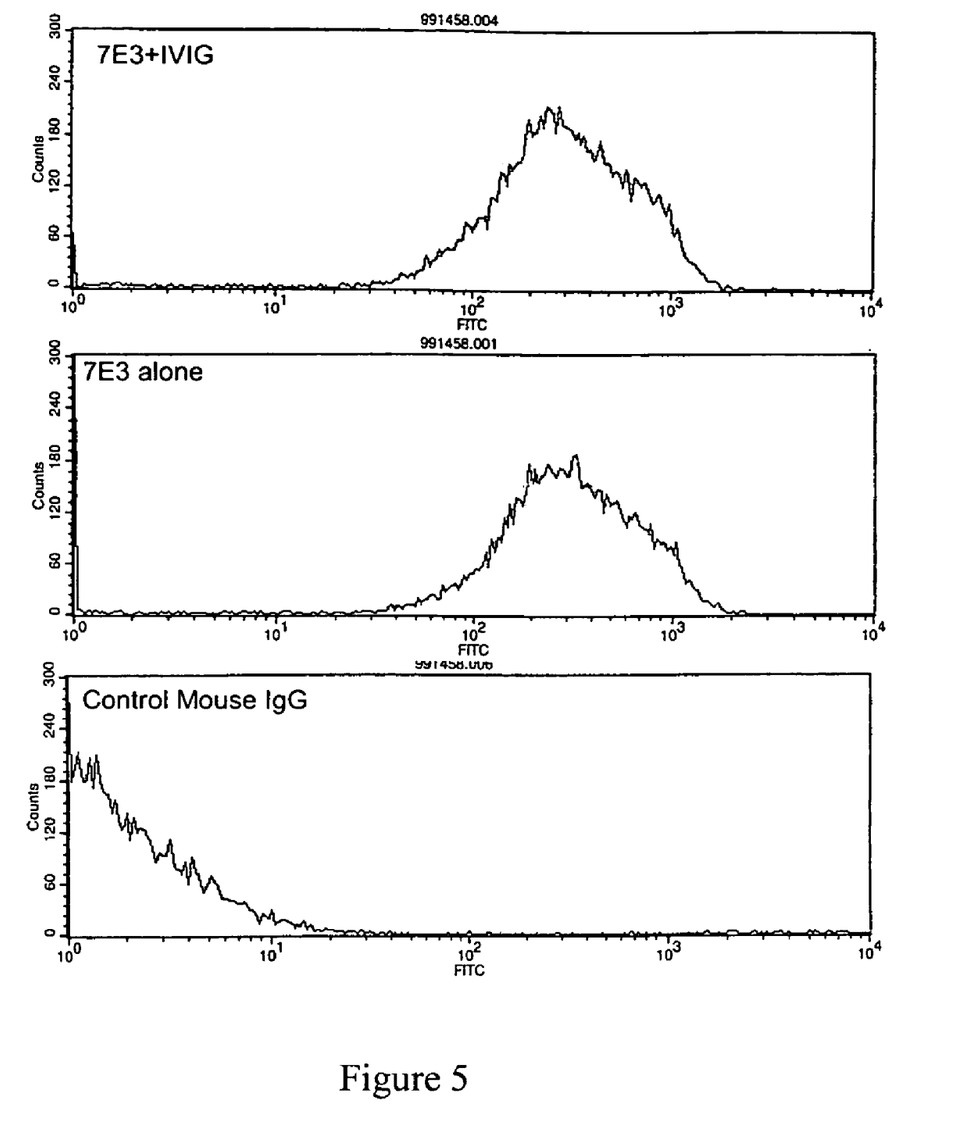
FIG. 5. IVIG effects on 7E3-platelet binding as determined by flow cytometry. 7E3 was incubated with human platelets in the presence or absence of IVIG. The histograms plot platelet count verses relative fluorescence intensity. The bottom panel shows the fluorescence histogram obtained for control mouse IgG incubated with platelets (median fluorescence intensity (MFI) was 1.3). The middle panel shows 7E3 incubated with platelets (MFI=246), and the top panel shows 7E3 incubated with platelets in the presence of IVIG (MFI=284). No decrease in MFI was observed for 7E3 binding to platelets in the presence of IVIG.
Figure 6:
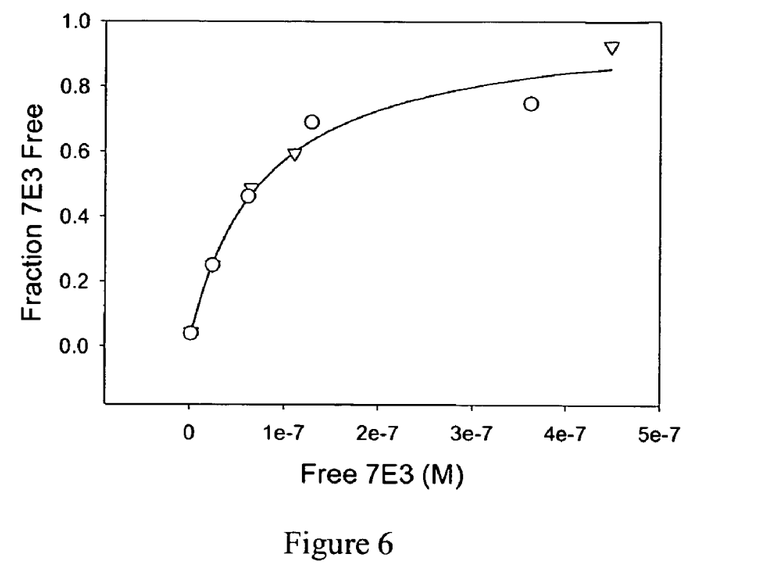

Results of the qualitative flow cytometric analyses are shown in FIG. 5. No shift in the fluorescence histogram was observed in the presence of IVIG. Results from the quantitative studies are shown in FIG. 6. Binding curves are nearly identical in the presence and absence of IVIG. No significant difference was found in the binding parameters $K_A$, and $R_t$. Without IVIG present, KA was 4.9±0.7×10$^8$ M$^{-1}$ and $R_t$ was 7.5±0.4×10$^{-8}$ M (55 000±3000 GP/platelet). With IVIG, KA was 5.5±1.2×10$^8$ M$^{-1}$ and $R_t$ was 7.6±0.7×10$^{-8}$ M (56 000±5000 GP/platelet).

Example 6

In this example, the effect of IVIG on the clearance of anti-platelet antibodies was studies in FcRn knock-out mice. β-2-microglobulin knockout mice (lacking FcRn expression) and C57B1/6 control mice, 21-28 g, were obtained from Jackson Laboratories (Bar Horbor, Me.). Mice, 3-5 per group, were dosed via the jugular vein cannula with either IVIG (1 g/kg) or saline, followed by 8 mg/kg 7E3. Blood samples, 20 μl per time point, were obtained from the saphaneous vein of the mice over the course of four days for the knockout mice, and over the course of 30 to 60 days for the control mice. Plasma 7E3 concentrations were determined by ELISA as described in Example 2.

Standard non-compartmental pharmacokinetic analyses were performed to determine the clearance and terminal half life of 7E3 for the various treatment groups (11), using WIN-NONLIN software (Pharsight Corp., Palo Alto, Calif.). Unpaired T-tests were performed using GraphPad Instat (GraphPad Software, Inc., San Diego, Calif.).

Figure 7:
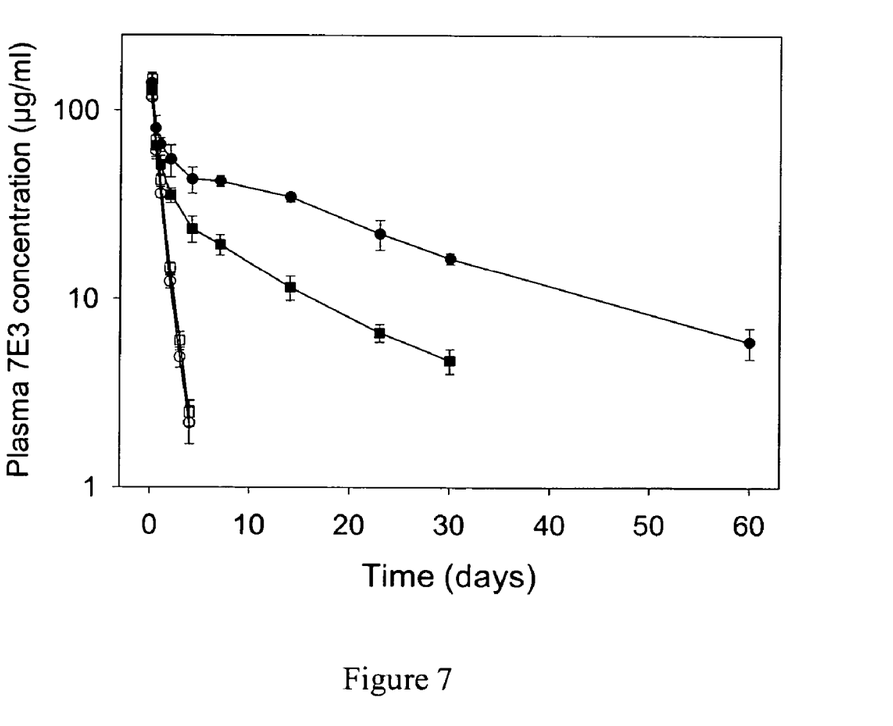
FIG. 7. 7E3 pharmacokinetics following IVIG treatment in control and FcRn-deficient mice. Mice (3-5 per group) were dosed intravenously with IVIG (1 g/kg) followed by 7E3 (8 mg/kg). Treatment groups are designated as follows: 7E3+saline in control mice (●); 7E3+IVIG in control mice (■); 7E3+saline in knockout mice (○); and 7E3+IVIG in knockout mice (□). 7E3 concentrations were determined via ELISA. Error bars represent the standard deviation about the mean concentration at each time point. IVIG treatment significantly increased the clearance of 7E3 in control mice (p<0.001), but not in FcRn-deficient mice.

IVIG's effects on 7E3 pharmacokinetics in B-2-microglobulin knock-out and control C57BL/6 mice are shown in FIG. 7, where it can be seen that IVIG increases the clearance of 7E3 in control mice (P<0.0001), and IVIG treatment failed to increase the clearance of 7E3 in the mice lacking FcRn expression (see Table 2), thus establishing that IVIG's effects on anti-platelet antibody clearance are mediated via the FcRn receptor.

TABLE 2

| Group | CL of 7E3 (ml d$^{-1}$ kg$^{-1}$) | $t_{1/2}$ (d) |
|---|---|---|
| Control mice-7E3 alone | 5.2 ± 0.3 | 20 ± 2 |
| Control mice-7E3 + IVIG | 14.4 ± 1.4 | 12 ± 2 |
| knockout mice-7E3 alone | 72.5 ± 4.0 | 0.78 ± 0.07 |
| knockout mice-7E3 + IVIG | 61.0 ± 3.6 | 0.75 ± 0.05 |

Non compartmental techniques were used to determine each parameter value. Values are listed as mean ± standard deviation (n = 3–5).

Example 7

Figure 8:
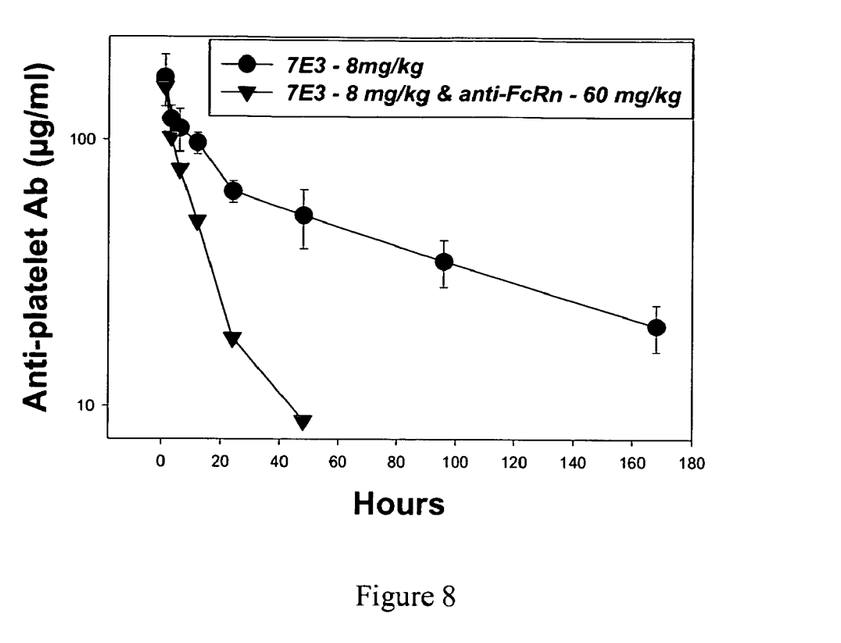
FIG. 8. Alteration of anti-platelet antibody pharmacokinetics following the administration of an anti-FcRn monoclonal antibody. Rats were dosed intravenously with a monoclonal anti-platelet antibody (7E3, 8 mg/kg), with or without pre-treatment with a monoclonal anti-FcRn antibody (4C9, 60 mg/kg). Black circles represent 7E3 plasma concentrations observed in animals receiving 7E3 alone (n=4), and red triangles represent 7E3 plasma concentrations observed in a rat that was pretreated with monoclonal anti-FcRn antibody (administered intravenously 4.5 h prior to 7E3 dosing). As shown, pretreatment with monoclonal anti-FcRn antibody led to a dramatic increase in the elimination of the anti-platelet antibody (i.e., 7E3 clearance was increased by 400%). 7E3 concentrations were determined via ELISA. Error bars represent the standard deviation about the mean concentration at each time point.

An example of an agent suitable to specifically inhibit binding of anti-platelet antibodies to FcRn receptors is a monoclonal anti-FcRn antibody. Hybridomas secreting monoclonal anti-FcRn antibodies were obtained from the American Type Culture Collection (ATCC#: CRL-2437, designation: 4C9). The hybridoma cells were grown in culture in standard media supplemented with 1% fetal bovine sera. Culture supernatant was collected, centrifuged, and subjected to protein-G chromatography to allow purification of IgG. As shown in FIG. 8, administration of ~60 mg/kg of the specific anti-FcRn antibody preparation led to a ~400% increase in the rate of clearance of an anti-platelet antibody in the thrombocytopenia animal model from Example 1. In contrast, in this same model, 2 g/kg of IVIG leads to only a ~100% increase in antiplatelet antibody clearance. This demonstrates the agent used to effect the clearance of 7E3 in this Example, i.e., a specific inhibitor of FcRn, is more potent and more effective than IVIG, which is considered to be a non-specific inhibitor of FcRn.

Example 8

This embodiment describes the effects of 4C9 on another antibody, AMI. Female Sprague Dawley rats, 175-275 g, were instrumented with jugular vein cannulas under ketamine/xylazine anesthesia (75/15 mg/kg). Two days following surgery, animals were treated with 0, 3, 15 and 60 mg/kg 4C9, which was injected via the jugular vein cannula (3-4 rats per group). Four hours after the administration of 4C9, AMI (8 mg/kg) was administered through the cannula, and blood samples (150 ul) were collected at 1,3,6,12,24,48, 72 and 96 hours. Cannula patency was maintained for flushing with approximately 200 ul heparinized saline. Blood was centrifuged at 13,000 g for 3-4 minutes and the plasma was isolated and stored at 4 C until analyzed. Plasma AMI concentrations were determined by ELISA.

Figure 9:
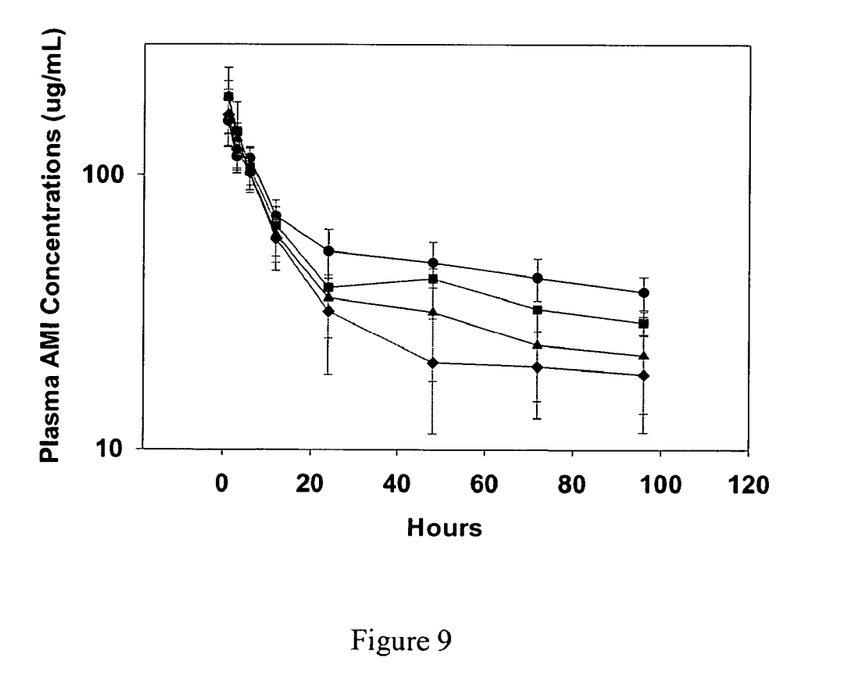

As shown in FIG. 9, the clearance of AMI increased by 99% following administration of 4C9 from 0.99±0.14 ml/h/kg in control animals to 1.97±0.49 ml/h/kg in animals pretreated with 60 mg/kg 4C9 (p<0.05). As such, these data demonstrate that an anti-FcRn antibody may be used to increase the clearance of IgG antibodies, in vivo.

Example 9

This example demonstrates the generation of monoclonal antibodies to the human FcRn. The light chain of human FcRn (i.e., human beta-2-microglobulin, Sigma Chemical, St. Louis, Mo.), emulsified in Freund's incomplete adjuvant (Sigma Chemical), was used to repetitively immunize six Balb/c mice (Harlan, Indianapolis, Ind.). Animals were bled from the saphenous vein 7-10 days after immunization, and antibodies directed against the human FcRn light chain were detected with an antigen capture enzyme-linked immunosorbent assay (ELISA). The animal with the highest ELISA response was selected for use as a splenocyte donor, and fusion was performed with murine SP20 myeloma cells (ATCC, Manassas, Va.). Briefly, the mouse was sacrificed with ketamine (150 mg/kg) and xylazine (30 mg/kg), and the spleen was rapidly removed using aseptic technique. Splenocytes were teased out of spleen tissue with the use of sterile 22-gauge needles, suspended in RPMI 1640, and fused with SP20 cells by centrifugation with polyethylene glycol, using standard techniques (e.g., as described in: Harlow E and Lane D. 1988. Antibodies: A laboratory manual. New York: Cold Spring Harbor Laboratory). Fused cells were selected through application of HAT selection medium (Sigma Chemical) and cloned by the method of limiting dilution. Tissue culture supernatant was assayed for anti-FcRn activity by evaluating ELISA response against human beta-2-microglobulin.

Figure 10:
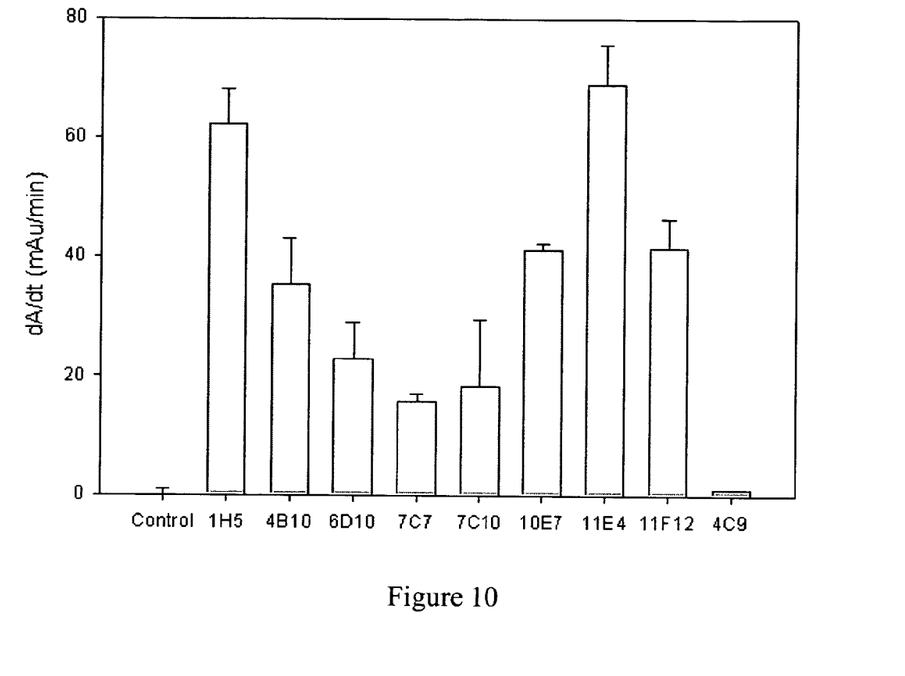

Ninety-one viable hybridoma clones were identified, and tissue culture supernatant was obtained from the culture of each clone to screen for the presence of anti-human FcRn light chain antibodies. Briefly, the human FcRn light chain was coated on 96-well microplates overnight at 4° C. Plates were then washed and incubated with either: phosphate buffered saline (PBS, as a negative control), culture supernatant obtained from the hybridomas, or with culture supernatant obtained from the culture of 4C9 hybridoma cells, which secrete antibodies directed against the light chain of rat FcRn (Raghavan et al., Immunity 1(4): 303-315, 1994). Following incubation for 2 h at room temperature, the plates were washed, and a goat anti-mouse Fab specific antibody conjugated with alkaline phosphate was added and incubated for 1 hr. Finally, plates were washed and p-Nitrophenyl phosphate was added. The change in absorbance with time (over 10 min) was monitored via a microplate reader at 405 nm. From the 91 viable potential anti-human FcRn clones, 8 positive clones were identified. These clones were 1H5, 4B10, 6D10, 7C7, 7C10, 10E7, 11E4 and 11F12. Their responses against the light chain of human FcRn are summarized in FIG. 10 (plotted is the net assay response; e.g., raw response minus the assay response for the PBS control). One-way ANOVA revealed significant differences in assay response ($p<0.0001$), and the assay responses for the 8 positive clones were found to be significantly different from that of the control ($p<0.01$ for each clone, Dunnett multiple comparison test). Additionally, this assay revealed that 4C9 antibodies, which are directed against the rat FcRn light chain, failed to show significant binding to the human FcRn light chain.

Example 10

This example describes the effect of anti-FcRn light chain antibodies on the binding of human IgG to 293 cells that express human FcRn. To demonstrate this, 293 cells expressing human FcRn were obtained from Dr. Neil Simister of Brandeis University. Human IgG was labeled with FITC by standard procedures. Tissue culture supernatant was obtained from cultures of four hybridomas (11E4, 11F12, 1H5, 10E7) that were found to secrete antibodies directed against the light chain of human FcRn (Example 9).

293 cells were treated with trypsin:EDTA and suspended in medium. The cell suspension was centrifuged at 300 g for 5 min, re-suspended in buffered saline, and cells were counted by a hemocytometer. Approximately $3.6 \times 10^6$ cells/ml of 293 cells were added to each centrifuge tube within buffered saline at pH 6 or 8. Cells were incubated with buffered saline alone, or with FITC-IgG at a concentration of 1 µg/ml in the presence or absence of cell culture supernatant obtained from the hybridoma cells. The reaction mixture was incubated at room temperature for 1.5 h, and cells were then washed and re-suspended in buffered saline. Cell-associated fluorescence was analyzed with a fluorometer, with excitation and emission wavelengths set at 494 and 520 nm, respectively.

Consistent with the known pH dependent binding of human IgG to human FcRn, the cell-associated fluorescence was found to be 253000 and 10800 for 293 cells incubated with 1 µg/ml FITC-human-IgG at pH 6.0 and 8.0, respectively. In contrast, for cells incubated in the absence of FITC-IgG, cell associated fluorescence was found to be 5220 and 5300 at pH 6.0 and 8.0, respectively. For cells incubated at pH 6.0 with FITC-IgG and the culture supernatant obtained from cells secreting anti-FcRn antibodies, cell associated fluorescence was decreased by 80-84% (see Table 3, below).

TABLE 3

293 cell-associated fluorescence after incubation with human FITC-IgG and potential inhibitors

| | FITC-IgG (µg/ml) | | | | | |
| --- | --- | --- | --- | --- | --- | --- |
| | 0 | 1 | 1 | 1 | 1 | 1 |
| Positive clones | N/A | N/A | 11E4 | 1H5 | 11F12 | 10E7 |
| PH = 6 | 5222 | 253465 | 49904 | 49751 | 40230 | 39750 |
| PH = 8 | 5302 | 10881 | | | | |

N/A indicates not applicable.

These results indicate that the binding of human IgG to 293 cells expressing human FcRn is pH dependent, with much greater binding shown at ph 6.0 relative to that seen at pH 8.0. Culture supernatant from hybridomas secreting antibodies directed against the human FcRn light chain are able to inhibit the binding of human IgG to FcRn.

Example 11

This example further demonstrates that the antibodies of the present invention are non-competitive inhibitors of IgG binding to FcRn. Binding of mouse IgG to 293 cells expressing hFcRn was determined in the presence or absence of the anti-hFcRn antibodies was determined as follows. 293 cells were incubated with PBS, with cell culture supernatant from two hybridomas that were identified as secreting anti-human FcRn light chain antibodies, and with cell culture supernatant obtained from cells secreting monoclonal anti-methotrexate mIgG1 (AMI, as a negative control). This incubation was performed in duplicate, with or without co-incubation with human IgG (1 mg/ml). Following this incubation, the cells were incubated with an anti-mouse IgG antibody labeled with FITC (i.e., to detect the presence of murine anti-FcRn antibody bound to human FcRn on the surface of the 293 cells). Cells were washed and cell associated fluorescence was assessed via a fluorometer. All incubations were performed at pH 7.4.

Figure 11:
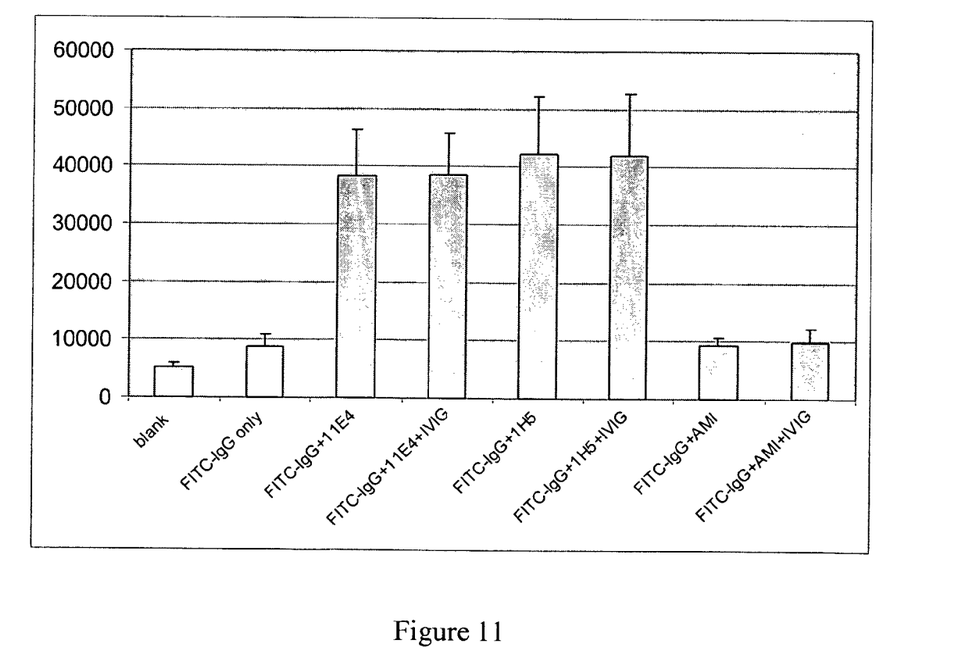
FIG. 11. Effect of presence of IgG on the reactivity of anti-hFcRn against FcRn. 293 cells expressing hFcRn were incubated with anti-FcRn antibodies with or without human IgG. Binding was detected by second antibody conjugated to FITC. Cell fluorescence was assessed by a fluorometer.

The results (FIG. 11) show significant binding of mouse IgG to 293 cells expressing hFcRn following the incubation of cells with culture supernatant from hybridoma cells (11E4 & 1H5 from Example 9). These binding data show that co-incubation with human IgG did not lead to a significant change in the assay response, which is consistent with "non-competitive" binding (i.e., where the apparent affinity of the anti-FcRn antibodies for hFcRn is not altered by the presence of the natural ligand—human IgG).

Also shown are results from incubation of the 293 cells with supernatant from cells that secrete murine monoclonal IgG1 antibodies directed against methotrexate (i.e., as a negative control). Incubation of the 293 cells with the anti-methotrexate antibody did not lead to a significant assay response. This is (again) consistent with the hypothesis that specific anti-hFcRn antibodies are responsible for the significant binding observed following incubation of cells with 11E4 & 1H5 supernatant.

Example 12

Figure 13:
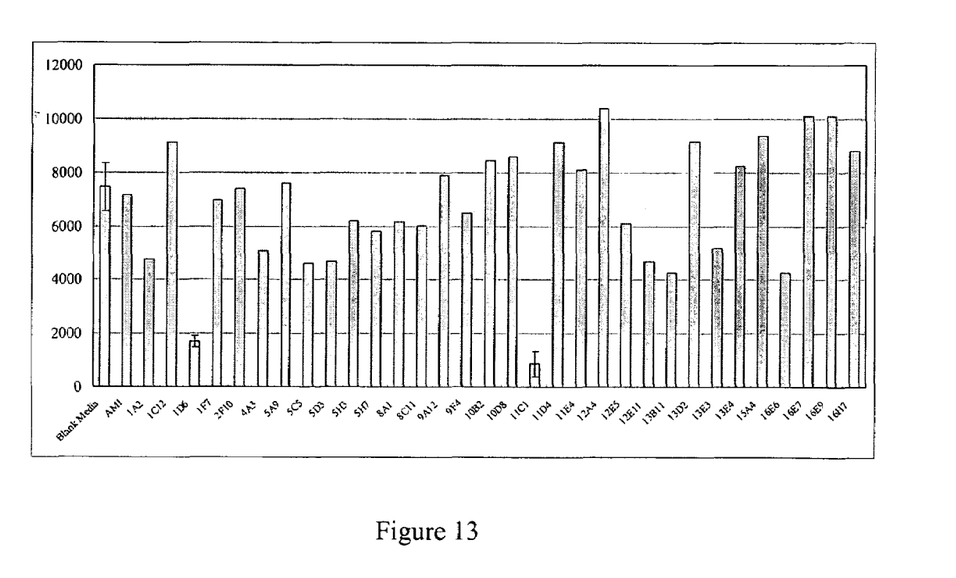
FIG. 13. Binding of human IgG to 293 cells expressing human FcRn is reflected through the sample fluorescence (as indicated on the y-axis). Tissue culture supernatant obtained from hybridoma clones 1D6 and 11C1 demonstrated a highly significant inhibition of human IgG binding to the 293 cells at pH 6.0.

This example describes the generation of monoclonal antibodies with specificity for human FcRn. The peptide sequence GEEFMNFDLKQGT (Invitrogen Corp., Carlsbad, Calif.), selected from the primary sequence of the human FcRn heavy chain, was conjugated with keyhole limpet hemocyanin (KLH) (Pierce Biotechnology Inc., Rockford, Ill.), emulsified in Freund's incomplete adjuvant (Sigma Chemical) and used to repetitively immunize six Balb/c mice (Harlan, Indianapolis, Ind.). Animals were bled from the saphenous vein 7-10 days after immunization, and antisera were assessed for activity in inhibiting the binding of human IgG to cells expressing human FcRn with a cell binding assay. Briefly, serum samples from the animals were incubated with 293 cells expressing human FcRn and with 50 µg/ml FITC-labeled human IgG, at pH 6, 37° C., for 2 hours. The mixture was then centrifuged at 250 g for 5 minutes and the cells were washed with PBS at pH 6. After centrifugation, the cells were resuspended in PBS at pH 7.4. Fluorescence was assessed by fluorometry. The excitation and emission wavelength were set at 494 and 520 nm respectively. The animal associated with the anti-sera demonstrating maximum inhibition of the fluorescence signal was selected for use as a splenocyte donor. Spleen cells were obtained and fused with murine SP20 myeloma cells (ATCC, Manassas, Va.). Briefly, the mouse was sacrificed with ketamine (150 mg/kg) and xylazine (30 mg/kg), and the spleen was rapidly removed using aseptic technique. Splenocytes were teased out of spleen tissue with the use of sterile 22-gauge needles, suspended in RPMI 1640, and fused with SP20 cells by centrifugation with polyethylene glycol, using standard techniques (e.g., as described in: Harlow E and Lane D. 1988. Antibodies: A laboratory manual. New York: Cold Spring Harbor Laboratory). Fused cells were selected through application of HAT selection medium (Sigma Chemical) and cloned by the method of limiting dilution. Tissue culture supernatant was assayed for inhibition of the binding of human IgG to 293 cells expressing human FcRn, using an approach modified from that described above. Thirty-two viable hybridoma clones were identified, and tissue culture supernatant was obtained from the culture of each clone to screen for the presence of anti-human FcRn antibodies. Briefly, tissue culture supernatants from all the viable clones were incubated with human FcRn-transfected 293 cells and 30 µg/ml FITC-labeled human IgG at pH 6, 37° C., for 2 hours. After incubation, the cells were washed and then resuspended in PBS at pH 7.4. Sample fluorescence was analyzed by fluorometry. From the 32 viable potential anti-human FcRn clones, 2 positive clones were identified. These clones were 1D6 and 11C1 (FIG. 13). One-way ANOVA revealed significant differences in assay response (p<0.0001), and the assay responses for the 2 positive clones were found to be significantly different from that of the control (p<0.01 for each clone, Dunnett multiple comparison test). Additionally, this assay revealed that AMI antibody, which is a negative control, murine IgG1 antibody with high affinity for methotrexate, failed to inhibit the binding of human IgG to the human FcRn-transfected 293 cells.

Example 13

Figure 12:
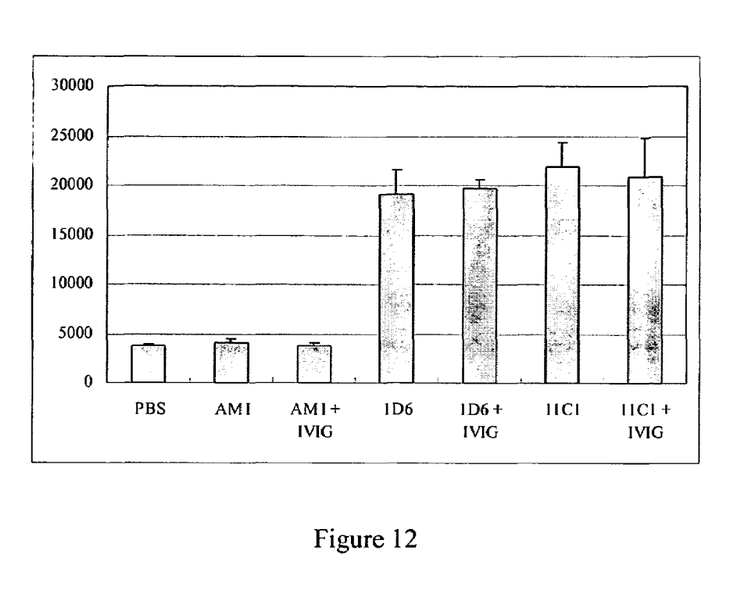
FIG. 12. Effect of presence of IgG on the reactivity of anti-hFcRn (heavy chain) against FcRn. 293 cells expressing hFcRn were incubated with anti-hFcRn (heavy chain) antibodies with or without human IgG. Binding was detected by second antibody conjugated to FITC. Cell fluorescence was assessed by a fluorometer.

In order to test whether 1D6 or 11C1 bind to human FcRn (hFcRn) non-competitively (i.e., with respect to human immune globulin), culture supernatant from W8 (control), 1D6, and 11C1 were incubated with hFcRn-transfected 293 cells at pH 7.4 and 37° C. for 2 hours with or without the presence of 1 mg/ml of pooled human immune globulin (IVIG, Gamunex®, Bayer). After washing and centrifugation, the 293 cells were incubated with 100 µg/ml FITC-labeled goat anti-mouse IgG at pH 7.4 and 37° C. for 1.5 hours. Cells were washed and centrifuged, and cell-associated fluorescence was analyzed by fluorometry. The results are presented in FIG. 12 (n=3).

The data demonstrate that high concentrations of human immune globulin do not inhibit the binding of hFcRn-transfected cells to 1D6 or 11C1. As such, these data support the hypothesis that both 1D6 and 11C1 bind to hFcRn in a non-competitive manner (relative to pooled human IgG).

Example 14

This example describes the evaluation of 1D6 and 11C1 binding to human beta-2-microglobulin to further support that 1D6 and 11C1 are directed against the heavy-chain of FcRn. To evaluate this, human beta-2-microglobulin (b2m, 3 ug/ml in phosphate buffer, 250 ul) was used to coat wells of 96-well microplates. Plates were incubated at 4 C overnight. Plates were then washed with phosphate-buffered saline and DDW. Culture supernatant from 11E4 (anti-human beta-2-microglobulin), 4C9 (anti-rat beta-2-microglobulin), 1D6, and 11C1 were added into the plates and incubated at room temperature for 2 hours. Plates were washed with PBS and DDW. Goat-anti-mouse IgG-alkaline phosphatase conjugate (1:500 in phosphate buffer, 250 ul) was added to the plates and plates were incubated for 1 hour at room temperature. Plates were washed with phosphate buffered saline and DDW. para-nitro-phenyl-phosphate in DEA buffer (4 mg/ml, 200 ul) was added to the plates and absorbance at 405 nm was monitored for 10 min via plate reader.

The results are shown in the table 4 below.

TABLE 4

| Supernatant | | | | Mean | SD |
| --- | --- | --- | --- | --- | --- |
| 4C9 | 28.426 | 33.249 | 35.163 | 32.279333 | 3.4715965 |
| 1D6 | 6.366 | 5.689 | 6.14 | 6.065 | 0.3446752 |
| 11C1 | 7.371 | 7.343 | 6.137 | 6.9503333 | 0.7045064 |
| 11E4 | 576.514 | 533.44 | 509.663 | 539.87233 | 33.886505 |

ANOVA shows significant difference between groups (P < 0.0001)
Tukey post t test shows significant differences between 11E4 and all other IgGs (P < 0.001) post t test shows no difference between 4C9, 1D6, and 11C1

Example 15

This example describes the construction and expression of mouse/human chimeric antibodies. Total RNA was prepared from pelleted hybridoma cells that express 1D6 and 11C1 monoclonal antibodies via the SV total RNA isolation system (Promega). cDNA was synthesized using oligdT primers and reverse transcriptase (Invitrogen). The variable regions of the 1D6 heavy chain and light chain were amplified from first-strand cDNA using Taq DNA polymerase with 35 cycles of PCR (1 cycle is 1 min at 93° C., 30 seconds at 45° C., and 1 min at 72° C.). The variable regions of the 11C1 heavy chain were amplified from first-strand cDNA using Taq DNA polymerase with 35 cycles of PCR (1 cycle is 1 min at 93° C., 30 seconds at 56° C., and 1 min at 72° C.). The variable regions of the 11C1 light chain were amplified from first-strand cDNA using Taq DNA polymerase with 35 cycles of PCR (1 cycle is 1 min at 93° C., 30 seconds at 60° C., and 1 min at 72° C.). All the PCR products were purified and cloned into PCR2.1-TOPO vector.

The PCR2.1-TOPO vector containing the variable regions of 1D6 and 11C1 was sequenced and the results were confirmed by alignment analysis. The baculovirus cassette vector, pAC-K-CH$_3$ was used to clone the heavy and light chain genes of variable regions. To clone the variable regions into pAC-K-CH$_3$ vector, the heavy chain variable regions were amplified by PCR using the primers containing XhoI and NheI cutting sites; the light chain variable regions were amplified by PCR using the primers containing SacI and HindIII cutting sites. The pAC-K-CH$_3$ containing the variable regions of both heavy chain and light chain were sequenced to confirm the insertion. The alignment analysis indicated that heavy chain and light chain were all ligated into pAC-K-CH$_3$ vector.

The pAC-K-CH$_3$ containing the variable regions of both heavy chain and light chain and linearized baculovirus DNA were co-transfected into Sf9 insect cells. Recombinant baculoviruses were prepared by homologous recombination using the BaculoGold

What is claimed is:

1. An isolated antibody or a fragment thereof which binds to human FcRn, is generated against heavy chain of human FcRn or a fragment thereof, functions as a non-competitive inhibitor of IgG binding to human FcRn and does not bind beta-2-microglobulin, and wherein the antibody or the fragment thereof binds with specificity to a peptide consisting of the sequence GEEFMNFDLKQGT (SEQ ID NO:1).

2. The antibody of claim 1, wherein the antibody is a murine antibody.

3. The antibody of claim 1, wherein the antibody is selected from the group consisting of polyclonal and monoclonal.

4. The antibody of claim 1, wherein the antibody is chimeric or humanized.

5. The antibody fragment of claim 1, wherein the fragment is selected from the group consisting of Fab, F(ab)'$_2$, Fv and ScFv.

6. The antibody of claim 1, wherein binding to FcRn is independent of the pH over a pH range of 6.0 to 8.0.

7. The antibody of claim 3, wherein the antibody is a monoclonal antibody.

8. A method for reducing binding of IgG to FcRn in an individual comprising the steps of providing an isolated antibody or a fragment thereof which binds to human FcRn, is generated against heavy chain of human FcRn or a fragment thereof, is a non-competitive inhibitor of IgG binding to human FcRn and does not bind beta-2-microglobulin, and wherein the antibody or the fragment thereof binds with specificity to a peptide consisting of the sequence GEEFMNFDLKQGT (SEQ ID NO:1; and administering the antibody or the fragment thereof to an individual in an amount sufficient to inhibit the binding of IgG to FcRn in the individual.

9. The method of claim 8, wherein the individual has an autoimmune or alloimmune disease.

10. The method of claim 9, wherein the autoimmune disease is immune thrombocytopenia.

11. The method of claim 10, wherein the individual is a human.

12. The method of claim 8, wherein the antibody is administered at a dosage of 1 mg/kg to 2 g/kg.

13. The method of claim 12, wherein the antibody is administered at a dosage of 1 mg/kg to 200 mg/kg.

* * * * *